United States Patent
Reed, Jr.

[11] 4,001,191
[45] Jan. 4, 1977

[54] COMBUSTIBLE MONOMERS AND POLYMERS THEREFROM

[75] Inventor: Samuel F. Reed, Jr., Huntsville, Ala.

[73] Assignee: Rohm and Haas Company, Philadephia, Pa.

[22] Filed: Oct. 18, 1960

[21] Appl. No.: 63,443

Related U.S. Application Data

[63] Continuation-in-part of Ser. No. 785,523, Jan. 7, 1959, abandoned.

[52] U.S. Cl. .................. 260/77.5 BB; 149/19.91; 149/22; 260/467; 260/482 B; 260/482 C; 260/606.5 B
[51] Int. Cl.² ........................................ C08F 18/24
[58] Field of Search ............. 260/77.5, 482 C, 467, 260/606.5, 77.5 BB, 482 B Primary Examiner—Leland A. Sebastian

EXEMPLARY CLAIM

2. Carbamates of the general formula:

$$R-NH-C(=O)-OR',$$

in which R is selected from the group consisting of $$CH_2=CH-C(=O)-,$$

and $$CH_2=C(CH_3)-C(=O)-,$$

and R' is selected from the group consisting of $$(CH_2ONO_2)_3C-CH_2-,$$

$$(C_2B_{10}H_{11}-CH_2)_2CH-,$$

$$(C_2B_{10}H_{11})_2CH-,$$

and $$C_2B_{10}H_{11}(CH_2)_n-,$$

in which n is 1 to 4. 15. A copolymer of at least one of the monomers of claim 2 with at least one monomer selected from the group consisting of methyl acrylate, ethyl acrylate, butyl acrylate, 2-ethylhexyl acrylate, the higher alkyl esters of methacrylic and ethacrylic acids and mixtures thereof.

15 Claims, No Drawings

COMBUSTIBLE MONOMERS AND POLYMERS THEREFROM

This application is a continuation-in-part of Ser. No. 785,523 filed Jan. 7, 1959, now abandoned.

This invention concerns combustible polymerizable monomeric carbamates and the polymers formed by the polymerization thereof. More particularly, the invention concerns high energy carbamate monomers which are valuable as binders for propellant grains.

High energy compounds, such as polynitrato compounds and boron-containing compounds, are frequently used as components of combustible or explosive compositions used as propellants for missiles, and rockets, etc. Generally, however, such compounds do not react chemically with the other components of the propellant charge and so are only physically dispersed therein. While it would be possible to incorporate stable boron compounds into propellant compositions without chemically reacting the boron compounds with the other components or the propellant charge, there are serious limitations on the amount of a boron-containing compound which can be incorporated if it does not react to form a polymeric compound with good physical properties. There are definite lower limits to the physical properties which a propellant grain must possess, and, because of the necessity for using high proportions of an oxidizer such as ammonium perchlorate, many of the propellant grains presently used are not substantially above these minimum requirements. Thus the addition of any appreciable amount of boron-containing compounds which did not contribute to the physical strength of the grain is frequently impossible. Boron-containing compounds which would yield polymers having good physical properties by polymerization or by condensation reactions would therefore be most desirable. Particularly desirable would be compounds which, while supplying the high energy requirements, would also chemically react to contribute to the desired physical properties required in such propellant charges or grains.

Suitable solid propellant grains generally require the presence of a binder which is elastomeric in nature to impart to the grain the required physical properties. A variety of elastomeric compounds have been employed with varying degress of success. Polysulfide rubber compounds have been employed, but they result in propellant charges with low specific impulse and have the further disadvantage that aluminum powder cannot be incorporated in said charges because of reaction of the aluminum powder with the sulfide groups. Polyurethane elastomers have also been employed, but they too have relatively low specific impulse and suffer the additional advantage of being hygroscopic, adsorbing moisture on storage.

One preferred method of preparing propellant grains consists in using as a binder a polymerizable monomer which, in the monomeric form, at casting temperatures, is a low viscosity liquid. The components of the propellant grain are mixed with the monomeric binder, the mixture is cast into molds and subsequently cured to produce the final propellant. It is also possible to store the propellant in the uncured form and cast in the desired shape later, but some compositions require the addition of a polymerization inhibitor in order to obtain satisfactory storage life.

A method has long been sought for chemically combining a high energy compound with a polymerizable monomer to produce a reaction product which, when polymerized, would function as a binder for propellant grains.

An object of this invention is to provide a high energy compound which, when polymerized, will also function as a binder for propellant grains.

It has been found that polymerizable materials which exhibit high energy contents and which will function as binders for propellant grains result when isocyanates containing polymerizable vinylidene groups are reacted with alcohols with high energy content. There result carbamates which, alone or in admixture with other materials, can be polymerized to give polymers with much desired physical properties.

Suitable isocyanates containing polymerizable vinylidene groups, include vinyl isocyanate, acryloyl isocyanate and methacryloyl isocyanate. Acryloyl isocyanate was prepared using acryloyl chloride and silver isocyanate according to the method of Lieser and Kemmner (Chem. Ber. 84, 4 (1951)) and the process is incorporated herein by reference. The methacryloyl isocyanate was prepared in a similar fashion. Vinyl isocyanate was prepared by the method of Hart (R. Hart, Bull. Soc. Chim. Belg. 65, 291 (1956)), as hereinafter set forth. The methods of preparation set forth in these publications are incorporated herein by reference.

Alcohols with high energy content include trinitratopentaerythritol (commonly referred to as "petrin") and the following boron-containing alcohols:

| | |
|---|---|
| bis(dekenylmethyl)carbinol | $(C_2B_{10}H_{11}-CH_2)_2CHOH$ |
| didekenyl-carbinol | $(C_2B_{10}H_{11})_2CHOH$ |
| dekenyl carbinol | $C_2B_{10}H_{11}CH_2OH$ |
| 2-dekenyl ethanol | $C_2B_{10}H_{11}(CH_2)_2OH$ |
| 3-dekenyl propanol-1 | $C_2B_{10}H_{11}(CH_2)_3OH$ |
| 4-dekenyl butanol-1 | $C_2B_{10}H_{11}(CH_2)_4OH$ |

As is obvious from the formulas, the alcohols employed in the present invention are high energy compounds, while the isocyanate supplies the unsaturation which permits polymerization of the carbamates which result from the interaction of the isocyanates and the alcohols.

These hydroxy dekenyl compounds can be prepared by a number of methods. Thus, bis(dekenylmethyl) carbinol can be prepared by reacting dekenylmethyl bromide with magnesium to form the Grignard complex (HĎCH$_2$MgBr) and reacting two moles of the Grignard complex with ethyl formate to form the carbinol. Didekenyl carbinol can be prepared by reacting acetylene with decaborane to form dekene, treating the dekene with phenyllithium to form the lithium dekene, and treating two moles of lithium dekene with one mole of ethyl formate to form didekenyl carbinol. Didekenyl carbinol can also be prepared by treating the acetate of diethynyl carbinol with decaborane and hydrolyzing the acetate of didekenyl carbinol so formed. Dekenyl carbinol can be prepared by reacting 3-acetoxypropyne-1 with decaborane to form dekenylmethyl acetate, followed by hydrolysis to form dekenyl carbinol. In the general formula HĎ(CH$_2$)$_n$OH, $n=2$ can be formed by treating 4-acetoxybutyne-1 and $n=3$ can be formed by treating 5-acetoxypentyne-1 using the same process set forth hereinbefore for 3-acetoxypropyne-1. These acetoxy acetylene derivatives are commercially available. The higher homologues can be prepared by the same process. The compounds $n=2$ and $n=3$ in the formula $H\emptyset(CH_2)_nOH$ can be prepared by an alternate process as follows: propargyle bromide (CH≡C—CH$_2$Br) is reacted with decaborane to form dekenylmethyl bromide. This bromide is reacted with magnesium to form the Grignard complex which is subsequently reacted with formaldehyde to form 2-dekenyl ethanol or with ethylene oxide to form 3-dekenyl propanol-1. Dimethyloldekene can be prepared by reacting 1,4-diacetoxybutyne-2 with decaborane to form bis(acetoxymethyl) dekene, and subsequently hydrolyzing the diacetoxy derivative to dimethyloldekene.

The carbamates of the present invention are prepared by adding alcohols with high energy content to the isocyanate with or without a catalyst such as ferric acetyl acetonate. The order of addition is not critical, but the reaction is exothermic, and portionwise addition of one component to the other is generally required in order to control the temperature of the reaction mixture.

The reaction temperature as such is not critical in that the reaction will occur over a very wide temperature range. Thus, the desired products have been obtained over a temperature range of about −60° C. to about 40° C. There are two factors, however, which govern the choice of reaction temperatures. At very low temperatures, the solubility of the reaction products in the solvent is substantially decreased, the products precipitate, and agitation difficulties are encountered. At temperatures near the upper temperature range, the portionwise addition must be very slow in order to control the exothermic heat. A preferred temperature range is from −10° to 20° C.

Because the isocyanates react readily with water, the reaction is conducted under anhydrous conditions; i.e., this means that there should not be more than 5 to 10 ppm. total of water present in all reactants since any water present will be removed by reaction with the isocyanate and result in loss of reactants. The reactants and the solvent, if one is employed, is carefully dried before use.

Although complete freedom from oxygen during the reaction period is not required, the preferred embodiment employs substantially oxygen-free conditions.

The molar ratios of the alcohol to the isocyanate can be varied and will obtain the desired product. Thus ratios of isocyanate to alcohol of from about 1.5 to 1.0 to 1.0 to 1.5 can be used. However, the reaction is quantitative at 1:1 ratio, and since any excess of either reagent must be removed during the purification of the product, a 1:1 ratio of alcohol to isocyanate represents the preferred embodiment.

The reaction between the alcohol and the isocyanate can be carried out in the absence of solvents, but difficulties are encountered with agitation and in dissipating the exothermic heat of reaction. The use of solvents represents the preferred emobodiment, since the solvents facilitate agitation and heat dissipation. Any inert solvent, i.e., solvents which do not react with the reactants or the reaction product, can be satisfactorily used. Thus hydrocarbons such as benzene and toluene, and chlorinated solvents such as chloroform, methylene chloride are satisfactory. Acetonitrile can also be used. diethyl ether has been employed, but, as set forth hereinafter, gives anomalous results, and so is not preferred. In the case of the solvents set forth hereinbefore, the reaction products precipitate as formed. Enough solvent is employed to give a readily stirrable reaction mixture. Because the solvent is required only for its physical effects, the ratio of solvent volume to the volume of the other reactants is not critical. Using 1 g. mole each of alcohol and isocyanate, however, 1 to 2 liters of solvent will accomplish the desired results.

The properties of the carbamates of the present invention can be altered by copolymerizing with comonomers. Suitable comonomers include methyl acrylate, ethyl acrylate, butyl acrylate, 2-ethylhexyl acrylate, and the higher alkyl esters of methacrylic and ethacrylic acids. Esters of this type include the butyl 2-ethylhexyl, decyl and lauryl esters of methacrylic and ethacrylic acids. The amount of these plasticizing esters used will depend on the other components of the propellant grain and the specific plasticizing monomer used. Generally, however, from 5 to 20% of plasticizing monomer, based on the weight of the carbamate, will provide the desired degree of plasticization.

While suitable physical properties can be obtained by copolymerizing the carbamates with other alkyl acrylates, the specific impulse developed by the propellant grain is decreased appreciably, particularly if the amount of the acrylate used be an appreciable portion of the grain. Another method of plasticizing polymers of the carbamates, which represents the preferred embodiments, uses nitrato esters of glycols as plasticizers. These nitrato esters are of themselves high energy compounds and so their use causes little reduction in the specific impulse of the grain. A particularly preferred compound of this type is triethylene glycol dinitrate.

It should also be understood that another embodiment of this invention can employ both methods of plasticization in one composition. Thus, a plasticizing comonomer as hereinbefore set forth can be employed in conjunction with plasticizing nitrato esters of glycols.

PROPELLANT FORMULATIONS

The carbamates of the present invention are useful as components of propellant compositions. The utility is demonstrated by typical propellant formulations in which plasticized acryloyl petrin carbamate is employed as the propellant binder.

15.0 gram (0.04 mole) acryloyl petrin carbamate (25% by weight)

15.0 gram triethylene glycol dinitrate (25% by weight)

0.2 gram (4 × 10$^{-4}$ mole) triethylene glycol diacrylate 0.008 gram (4 × 10$^{-5}$ mole) N-nitrosodiphenyl amine 30.0 gram ammonium perchlorate (50% by weight).

The above components with the exception of ammonium perchlorate were mixed at 85° C. in a 200 ml. three-necked flask fitted with mechanical stirrer and vacuum take-off. Within 3 – 4 minutes a liquid melt was obtained and the ammonium perchlorate was then added slowly with time allowed (5 minutes) for thorough mixing of all components. The flask was then degassed for a period of 2 – 3 minutes after which the melt was cast into a mold for curing. Cure time was twenty hours at 85° C. A tough plastic composition was obtained.

The use of lower ratios of monomer to plasticizer result in mixtures which are difficult to cast, particularly in the case where acryloyl petrin carbamate is a component. Lower ratios are cast satisfactorily with the other carbamates formed by the interaction of isocyanates containing polymerizable vinylidene groups with alcohols with high energy content. In addition, acryloyl petrin carbamate polymerizes satisfactorily in the absence of initiator whereas with the other carbamates, such as those derived from the boron-containing alcohols and isocyanates containing a polymerizable vinylidene group, 1% benzoyl peroxide or bis-azoisobutyronitrile are used as initiators. The ammonium perchlorate may be added in weight percentages up to 60% without causing difficulty in the casting operation. Caution should be observed in handling larger quantities of these materials under polymerization conditions.

The application of petrin carbamate monomers in propellant systems has been investigated. The technique of casting is similar to that described hereinbefore. The following are representative copolymer propellant formulations:

TABLE I

PROPELLANT FORMULATIONS FROM COPOLYMERS OF ACRYLOYL PETRIN CARBAMATE AND PETRIN ACRYLATE

|  | PA/APC No. 1 90/10 | PA/APC No. 2 80/20 | PA/APC No. 3 90/10 | PA/APC No. 4 80/20 | PA/APC No. 5 70/30 |
|---|---|---|---|---|---|
| Petrin acrylate (PA) | 43.88 g. | 39.00 g. | 43.88 g. | 39.00 g. | 34.13 g. |
| Acryloyl Petrin Carbamate (APC) | 5.52 g. | 11.04 g. | 5.52 g. | 11.04 g. | 16.56 g. |
| Triethylene glycol dinitrate | 49.40 g. | 50.01 g. | 21.17 g. | 21.44 g. | 21.72 g. |
| * Triethylene glycol diacrylate | 1.26 g. | 1.26 g. | 0.86 g. | 0.86 g. | 0.86 g. |
| Ammonium perchlorate (55 wt. %) | 116.18 g. | 122.32 g. | 86.09 g. | 87.18 g. | 88.47 g. |
| **Tensile strength (lbs./in$^2$) | 341,14,15 | 402,21,24 | 1009,44,40 | — | 915,60,52 |
| **Elongation % | 13,52,37 | 13,41,36 | 9,22,19 | — | 9,26,24 |
| Second Order Transition Temperature | −50° C. | −43° C. | −17° C. | −19° C. | −26° C. |

N-nitrosodiphenylamine was added in 0.1 mole percent concentrations to increase "pot-life" of the liquid melt.

* Triethylene glycol diacrylate added in concentrations of 3 mole percent (first two formulations) and 2 mole percent (last three formulations).
**The tensile strength and elongation values reported above were obtained at −40° F., 75° F. and 135° F. and are presented in that order in Table I.

In the above propellant formulations, the oxidizer, ammonium perchlorate, was 55 weight percent of the total mixture. The plasticizer, triethylene glycol dinitrate, made up 50 weight percent (No. 1 and No. 2 ) and 30 weight percent (Nos. 3, 4, and 5) of the plasticizer-monomer mixture. It is possible to obtain formulations employing any desired ratio of petrin acrylate to acryloyl petrin carbamate with oxidizer concentrations from 40–60 weight percent and plasticizer concentrations of from 30–50 percent. The other carbamates of the present invention may be substituted in the example above with comparably satisfactory results.

Other plasticizers will function satisfactorily in the formulations set forth hereinbefore, including such components as butanetriol trinitrate. Initiators may be added in low concentration, particularly with vinyl petrin carbamate to increase the rate of cure. Other oxidizers (i.e., ammonium nitrate) may be used as substitutes for ammonium perchlorate.

The following examples set forth certain well-defined embodiments of the application of this invention. They are not, however, to be considered as limitations thereof, since many modifications may be made without departing from the spirit and scope of this invention.

Unless otherwise specified, all parts are parts by weight. All temperatures are centigrade unless otherwise stated.

EXAMPLE I

Acryloyl Petrin Carbamate

Acryloyl petrin carbamate has been prepared from acryloyl isocyanate and petrin in either methylene chloride, acetonitrile of chloroform at temperatures ranging from −10° to 20° C. The reaction is highly exothermic requiring rapid agitation and intermittent cooling during the addition of petrin. It has been found that petrin of high purity (chromatographed petrin) gives the highest yeilds of acryloyl petrin carbamate.

The acryloyl isocyanate was prepared from acryloyl chloride and silver cyanate according to the method of Lieser & Kemmner (Chem. Ber. 84, 4 (1951)). It was then distilled through a vacuum line into a reaction vesel fitted with a mechanical stirrer, thermometer, dropping funnel and condenser equipped with drying tube (Drierite). The flask contained 1 liter of dry methylene chloride and had previously been cooled to −65° C. in an acetone-dry ice bath. To this solution, after warming to −10° C., 200-grams petrin was added dropwise with vigorous agitation and intermittent cooling using dry ice-acetone bath. The reaction conditions were controlled to the extent that the reaction temperature did not exceed 20° C. The reaction was extended 1 hour after the addition of petrin was complete, during which time the temperature of the mixture was allowed to approach room temperature. The solid which precipitated was filtered off and the filtrate concentrated to yield additional solid product. All portions of this product were combined and recrystallized from acetone-chloroform solution (¼ ratio). The yield of acryloyl petrin carbamate was 165 grams (60.5% based on petrin), m.p. 107° to 109° C. with polymerization.

Anal. Calc'd. for $C_9H_{12}N_4O_{12}$: C, 29.36; H, 3.26; N, 15.23; Vinyl, 7.34; $NO_3$, 50.54. Found: C, 29.51; H, 3.43; N, 14.73; Vinyl, 7.44; $NO_3$, 50.32.

The yield in the above described reaction was based on petrin used.

Acryloyl petrin carbamate has been characterized as follows:

FORMULA: $C_9H_{12}N_4O_{12}$

STRUCTURE:

$$CH_2=CH-\underset{\substack{\| \\ O}}{C}-\underset{\substack{| \\ H}}{N}-\underset{\substack{\| \\ O}}{C}-O-CH_2-\underset{\substack{| \\ CH_2ONO_2}}{\overset{\substack{CH_2ONO_2 \\ |}}{C}}-CH_2ONO_2$$

| | -continued |
|---|---|
| MOLECULAR WEIGHT: | 368 |
| MELTING POINT: | 107° C. with polymerization |
| IMPACT SENSITIVITY: | 24.3" 50% fire level (1 kg. weight) |
| HEAT OF EXPLOSION: | 630 cal./gram (exp.) |
| HEAT OF COMBUSTION: | 2835 cal./gram (exp.) |
| TALIANI: | Did not reach 100 mm. in six hours $m_{20_m} = 0.20$ $t_{20} = 72$ min. |

Acryloyl petrin carbamate polymerizes very readily on heating to its melting point and caution should be observed in carrying out large scale bulk polymerizations of this highly reactive monomer.

To a small test tube was introduced 1.0 gram of acryloyl petrin carbamate. The test tube was flushed several minutes with a slow stream of pre-purified nitrogen and stoppered. It was then placed in constant temperature bath at 110° to 115° C. The monomer melted and within one hour a hard glassy polymer was isolated. This polymer was insoluble in acetone and acetonitrile, both excellent solvents for poly(petrin acrylate).

The addition of 1.0 gram triethylene glycol dinitrate to the above yields a polymer with rubber-like character when the polymerization is conducted at 80° C. for a period of 2 hours. From 0.5 to 1.5 grams of triethylene glycol dinitrate have been added to one gram samples of acryloyl petrin carbamate to give flexible rubbery polymers at polymerization temperatures of from 65° to 90° C. Other compounds such as dimethyl adipate, dimethyl sebacate, triacetin, etc., also serve as plasticizers. The solution polymerization of acryloyl petrin carbamate has been carried out using benzoyl peroxide or azo-bis-isobutyronitrile at the one mole percent level.

To a 100 ml. flask was introduced a solution of 9.2 grams (0.025 mole) acryloyl petrin carbamate in 50 ml. dry acetonitrile. One mole percent benzoyl peroxide (0.041 gram) was added as polymerization initiator. The flask was flushed several minutes with a slow stream of nitrogen, stoppered, and placed in a constant temperature bath for a period of 24 hours. Fifty milliliters of ligroin was added to precipitate 7.23 grams of poly(acryloyl petrin carbamate).

The emulsion polymerization of acryloyl petrin carbamate was accomplished using the following recipe:
5.0 parts acryloyl petrin carbamate in 10 parts methyl ethyl ketone
20.0 parts distilled water
1.2 parts octylphenoxyethoxyethanol with 10–15 ethylene oxides per molecule
0.06 part ammonium persulfate Five grams acryloyl petrin carbamate was dissolved in 10 grams methyl ethyl ketone and added to a three-necked flask (in a 50° C thermostated bath) equipped with a nitrogen inlet tube, stirrer, and condenser with stopcock on top. Then 19.0 ml. of distilled water containing 1.2 grams octylphenoxyethoxyethanol with 10–15 ethylene oxides per molecule was added with moderate stirring. A slow stream of pre-purified nitrogen was passed over the stirred solution and out through the condenser (precaution taken to insure that the methyl ethyl ketone did not entrain out of the system) for a period of one hour. The condenser was lifted quickly and the initiator solution (0.06 gram ammonium persulfate in 1 ml. distilled water) was added to the system, the condenser replaced, and nitrogen flushed through the system for about 1 minute. The stopcock was then closed but a positive nitrogen pressure maintained on the system throughout the entire operation. Reaction time was eighteen hours. The polymerization was judged complete and the emulsion poured into a well-stirred solution of 500 ml. of methanol. A white precipitate appeared immediately. It was allowed to settle, collected by filtration, washed twice with methanol and air-dried. The yield was 3.2 grams (64%).

Copolymerization of acryloyl petrin carbamate with petrin acrylate[1], vinyl petrin ether[2], vinyl petrin carbamate and 2-ethylhexyl acrylate have been carried out in the presence of 30% triethylene glycol dinitrate as plasticizer. These copolymerizations were carried out on a test tube scale to give polymers of rubber-like character. Most of the comonomer mixtures contained 30 mole percent or greater of the acryloyl petrin carbamate. The copolymerization of a 50/50 mole percent mixture of acryloyl petrin carbamate and vinyl petrin carbamate illustrates the typical conditions for these copolymerizations.

[1]The preparation of petrin acrylate is described in Ser. No. 755,846, now U.S. Pat. No. 3,409,658, and Ser. No. 771,679, now U.S. Pat. No. 3,450,742, in the hands of a common assignee.
[2]The preparation of vinyl petrin ether is described in Ser. No. 779,503, now U.S. Pat. No. 3,427,295, filed DEC. 10, 1958, in the hands of a common assignee.

To a small test tube was added 3.68 grams (0.01 mole) acryloyl petrin carbamate, 3.40 grams (0.01 mole) vinyl petrin carbamate and 3.03 grams (30%) triethylene glycol dinitrate. The test tube was placed in a thermostated bath at 80° C. and a monomer melt obtained to which was added 0.0484 gram (1 mole percent) benzoyl peroxide in 1 ml. anhydrous ether via a pipette. After being flushed for several minutes with a slow stream of pre-purified nitrogen, the tube was tightly stoppered, the mixture thoroughly blended and the polymerization continued for a period of 24 hours. A firm rubber-like polymer was obtained.

The range of comonomer mixtures covered was from 90/10 to 50/50 with the exception of the acryloyl petrin carbamate/petrin acrylate where the entire range of comonomer compositions were covered. The use of triethylene glycol dinitrate at the 50% level gave extremely viscous liquid polymers when vinyl petrin carbamate or vinyl petrin ether were used as comonomers in compositions with mole ratios of 60/40 and 50/50.

EXAMPLE II

Vinyl Petrin Carbamate

Vinyl petrin carbamate is prepared from vinyl isocyanate and petrin using ferric acetylacetonate as catalyst.

Vinyl isocyanate was prepared from acryloyl chloride and sodium azide according to the following equation:

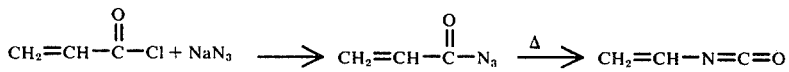

To a large 2-liter three-necked flask fitted with thermometer, mechanical stirrer, and dropping funnel containing 212 grams (0.782 mole) chromatographed petrin dissolved in 500 ml. dry chloroform and 5.0 grams ferric acetylacetonate at 0°–5° C. was added with rapid stirring 54.0 grams (0.782 mole) vinyl isocyanate. The vinyl isocyanate was added at such a rate that the temperature did not rise above 20° C. The reaction was allowed to continue for a period of 1 hour after the addition of the isocyanate. The solid precipitate which formed during this time was collected by filtration and washed thoroughly with ligroin. Ligroin was added to the filtrate (equal volume) to cause an additional quantity of precipitate to form. This was collected, washed thoroughly with ligroin and combined with the first portion. After recrystallization from acetone-chloroform (¼ by volume), 205 grams, (77%) m.p. 75° to 76° C. of vinyl petrin carbamate was obtained.

Anal. Calc'd. for $C_8H_{12}N_4O_{11}$: C, 28.23; H, 3.53; N, 16.45; $NO_3$, 54.7. Found: C, 28.27; H, 3.68; N, 15.71; Unsat., 7.88; $NO_3$, 53.88.

Pyridine has also been used as catalyst for this reaction but is somewhat less effective. Methylene chloride has also been used as solvent under similar conditions. Ethyl ether when used as solvent resulted in the isolation of a higher melting product (91° to 92° C.) which appears from all available data to be a polymeric form of vinyl petrin carbamate. This compound may also be isolated in high yields. Because of the formation of this polymeric material, ethyl ether is not a preferred solvent. No reaction is observed when vinyl isocyanate is added to petrin in the absence of catalysts.

Vinyl petrin carbamate may be polymerized in bulk by heating the monomer above its melting point (80° to 85° C.). Although the polymerization may be carried out in the absence of initiator, the rate is slow and it is preferred to add peroxide-type initiators (benzoyl peroxide) to hasten the polymerization.

To a small test tube was added 1.0 gram vinyl petrin carbamate and 0.01 gram benzoyl peroxide (via pipette using ether solution). The tube was flushed with pre-purified nitrogen, tightly stoppered and placed in an 85° C. constant temperature bath. The monomer melted to a clear colorless liquid, the liquid was stirred by hand to insure thorough mixing of initiator with monomer and polymerization continued for three hours. A glassy polymer was obtained. The polymer was soluble in acetone and acetonitrile.

Copolymerization of vinyl petrin carbamate with petrin acrylate and acryloyl petrin carbamate in the presence of the plasticizer triethylene glycol dinitrate has been successfully carried out. Monomer ratios (mole percent) of from 90/10 to 50/50 where vinyl petrin carbamate was the minor component have been investigated using 1 mole percent benzoyl peroxide as initiator. Polymerization time was 24 hours. Conversions were in the order of 95 to 100% in all cases.

To a small test tube containing 1.7 grams (0.005 mole) of vinyl petrin carbamate, 1.675 gram (0.005 mole) petrin acrylate and 0.845 gram (20%) triethylene glycol dinitrate was added 0.0242 gram (1 mole percent) benzoyl peroxide via pipette. The tube was flushed slowly with pre-purified nitrogen for 4 to 5 minutes, then tightly stoppered, placed in an 80° C. constant temperature bath. The monomers melted to give a clear liquid melt and polymerization was continued for a period of 24 hours. A polymer with rubber-like properties was obtained. Residual monomer analysis showed the vinyl petrin carbamate to be copolymerized to the extent of 98%.

In the same way, the dekenyl alcohols, set forth hereinbefore, in equimolar quantities, were substituted for petrin and the corresponding vinyl dekenyl carbamates were obtained.

EXAMPLE II

Methacryloyl Petrin Carbamate

Another high energy monomer prepared was methacryloyl petrin carbamate. It was thought that this monomer would be capable of undergoing polymerization in propellant formulations to give a system with acceptable physical properties. The monomer was prepared according to the reaction scheme

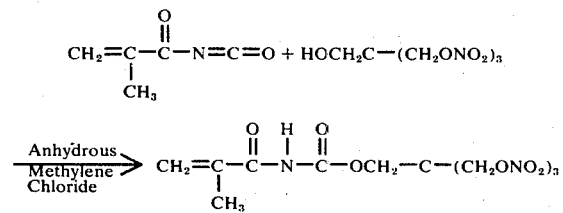

The methacryloyl isocyanate was prepared following the method of Lieser and Kemmner (from 100 grams silver cyanate and 50 grams (0.478 mole) methacryloyl chloride). It was then distilled through a vacuum line into a 500 ml. three-necked flask fitted with mechanical stirrer, dropping funnel, thermometer, and condenser containing 200 ml. of dry methylene chloride cooled in a dry ice-acetone bath at −70° C. The cooling bath was removed and the temperature raised to 0° to 5° C., at which point 140 grams (0.518 mole) petrin was added in small increments (5 to 10 ml.) while maintaining the reaction temperature below 10° C. by the intermittent application of an ice-water bath. A white solid precipitated from the reaction mixture during the addition. The reaction was continued for an overnight period. The product was collected by filtration and recrystallized from an acetone-chloroform mixture, m.p. 92° to 94° C. Yield of 40 grams (21.8%) was obtained (based on methacryloyl chloride used in the first step).

Anal. Calc'd. for $C_{10}H_{14}N_4O_{12}$: C, 31.45; H, 3.66; N, 14.64. Found: C, 31.77; H, 3.90; N, 14.48.

Methacryloyl petrin carbamate has been characterized as follows:

FORMULA: $C_{10}H_{14}N_4O_{12}$

-continued

| | |
|---|---|
| STRUCTURE: | $$CH_2=\overset{CH_3}{\underset{|}{C}}-\overset{O}{\underset{\|}{C}}-NH-\overset{O}{\underset{\|}{C}}-O-CH_2C-(CH_2ONO_2)_3$$ |
| MOLECULAR WEIGHT: | 382 |
| MELTING POINT: | 92° to 94° C. |
| IMPACT SENSITIVITY: | 25.3" at 50° fire level (1 kg. weight) |
| HEAT OF EXPLOSION: | 742, 734 cal./g. (exp.) |
| HEAT OF COMBUSTION: | 3159, 3183 cal./g. (exp.) |
| THERMAL STABILITY: | Did not end methyl violet paper test in 7 hr |
| TALIANI: | $M_{10_{mm}} = 0.07$ $t_{10_{mm}}$ 355 min. |

Methacryloyl petrin carbamate may be polymerized in bulk by heating the monomer slightly above its melting point (92° to 94° C.). Caution should be exercised during the bulk polymerization of relatively large quantities of this monomer which under certain conditions could lead to an explosion due to the rapid exotherm produced during polymerization. In most polymerizations, the rate of polymerization was much slower than the corresponding rate for acryloyl petrin carbamate.

To a small test tube was added 1.0 gram methacryloyl petrin carbamate and 0.01 gram benzoyl peroxide (via pipette using ether solution). The tube was placed under slight vacuum to remove the ether, flushed with pre-purified nitrogen, tightly stoppered and placed in a 100° C. thermostated bath. The monomer melted to a clear colorless liquid within 4–6 minutes, the test tube shaken by hand to insure thorough distribution of the initiator with monomer and the polymerization continued for a period of 3 hours. A hard glass-like polymer was obtained. The polymer was soluble in acetone; partially soluble in acetonitrile.

Copolymerizations of methacryloyl petrin carbamate with petrin acrylate, acryloyl petrin carbamate, vinyl petrin carbamate, vinyl petrin ether and 2-ethylhexyl acrylate were conducted in the presence of the plasticizer triethylene glycol dinitrate using 1 mole percent benzoyl peroxide as initiator. Monomer ratios (mole percent) of from 90/10 to 50/50 were examined where methacryloyl petrin carbamate was the major component. Polymerization time was 24 hours. Conversions were on the order of 94% to 98% in all cases. A typical copolymerization of a 50/50 mixture with petrin acrylate is described below.

To a small test tube containing 1.91 grams (0.005 mole) of methacryloyl petrin carbamate, 1.675 grams (0.005 mole) petrin acrylate and 0.707 gram (20%) triethylene glycol dinitrate was added 0.0242 gram (1 mole percent) benzoyl peroxide in ether solution via pipette. The tube was stripped of the ether under slightly reduced pressure, flushed slowly for 4–5 minutes with pre-purified nitrogen, then tightly stoppered and placed in a 90° C. thermostated oil bath. The monomers melted to give a clear liquid melt which after thorough mixing was allowed to polymerize during the course of a 24 hour period. A firm rubber-like polymer was obtained. This was typical of all polymers except those containing vinyl petrin ether in ratios lower than 80/20 which were obtained as viscous liquids.

Methacryloyl petrin carbamate can be polymerized in solution or emulsion under conditions similar to those used for acryloyl petrin carbamate.

EXAMPLE IV

Acryloyl Dekenylmethyl Carbamate

The interest in boron hydrides as possible additives to propellant systems has led to the development of a number of new and interesting monomers containing high percentages of boron. The search for high boron-containing monomers has further been accelerated by the discovery that decaborane reacts with acetylenic compounds to give what is thought to be a new type ring compound of the following formula:

$$B_{10}H_{14} + HC\equiv CH \rightarrow C_2B_{10}H_{12}$$

The nomenclature has been simplified to allow simple expression of the chemistry of these compounds. The compound will be known as dekene and a radical of dekene known as dekenyl.

| | | |
|---|---|---|
| $C_2B_{10}H_{12}$ | = | dekene |
| $C_2B_{10}H_{11}-$ | = | dekenyl |

One intermediate of interest which has previously been synthesized is hydroxymethyldekene. From this compound was prepared acryloyl dekenylmethyl carbamate through a reaction with acryloyl isocyanate.

$$CH_2=CH-\overset{O}{\underset{\|}{C}}-N=C=O + HOCH_2-H_{11}B_{10}C_2 \longrightarrow CH_2=CH-\overset{O}{\underset{\|}{C}}-NH-\overset{O}{\underset{\|}{C}}-OCH_2-H_{11}B_{10}C_2$$

A solution of 5.2 grams (0.057 mole) acryloyl isocyanate in 50 ml. dry methylene chloride was added to a solution of 9.7 grams (0.055 mole) hydroxymethyldekene in 50 ml. methylene chloride in a 200 ml. three-necked flask fitted with magnetic stirrer, reflux condenser, thermometer and dropping funnel at such a rate that the temperature did not exceed 30° C. An ice-water bath was employed for external cooling. After the addition was complete, the mixture was allowed to stand for 18 hours at room temperature with stirring. The mixture was then stripped free of solvent to yield a highly viscous liquid residue. The odor of the isocyanate was apparent. The residue crystallized on standing for approximately 20 minutes. The solid was recrystallized from pentane (only part of the material was soluble). The insoluble fraction was dried, m.p. 128° to 129° C. Yield was 9.08 grams (58.3%).

Anal. Calc'd. for $C_7H_{19}B_{10}NO_3$: C, 30.77; H, 6,96; B, 39.57; N, 5.13. Found: C, 31.60; H, 7.30; B, 36.17; N, 5.28.

The pentane soluble fraction was analyzed and found to be unreacted hydroxymethyldekene.

Acryloyl dekenylmethyl carbamate was found to polymerize on heating above its melting point. It was soluble in most common organic solvents so that solution polymerization presents little difficulty. It copolymerized well with petrin acrylate, acryloyl petrin carbamate and vinyl petrin carbamate. A typical copolymerization is described below.

To a small test tube was introduced 2.93 grams (0.01 mole) acryloyl dekenylmethyl carbamate, 3.25 grams (0.01 mole) petrin acrylate and 1.20 grams (20%) triethylene glycol dinitrate. To this mixture was added 1 mole percent benzoyl peroxide (0.0484 gram) in ether via pipette. After evaporation of the ether under slight vacuum, the test tube was flushed with pre-purified nitrogen, stoppered tightly, and placed in a 90° C. thermostated bath. A clear liquid melt was obtained within 5 minutes which polymerized to a firm rubber-like polymer during the following 6 hours.

In the same way, but with different quantities to compensate for the differences in equivalent weights, i.e. using equimolar quantities, bis(dekenylmethyl) carbinol, didekenyl carbinol, 2-dekenyl ethanol, 3-dekenyl propanol-1, and 4-dekenyl butanol-1 were reacted with acryloyl isocyanate to form the corresponding carbamates. The compounds obtained were very similar to the compound described hereinbefore and can be homopolymerized, copolymerized, etc. They are all high energy compounds, and can be used as hereinbefore described.

EXAMPLE V

Methacryloyl Dekenylmethyl Carbamate

The second in the series of monomeric compounds containing relatively high percentages of boron which was prepared was methacryloyl dekenylmethyl carbamate. This compound was prepared by reacting hydroxymethyldekene with methacryloyl isocyanate.

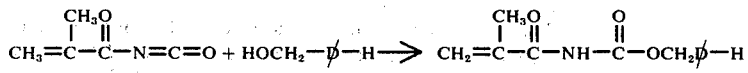

A solution of 4.2 grams (0.0378 mole) methacryloyl isocyanate in 40 ml. dry methylene chloride was added in small increments to a three-necked flask fitted with magnetic stirrer, reflux condenser with protective Drierite drying tube, thermometer and dropping funnel containing 6.2 grams (0.0353 mole) hydroxymethyldekene in 40 ml. dry methylene chloride. The reaction mixture was cooled in an icewater bath to maintain the temperature of the reaction at 20° C. or lower. After the addition, the reaction mixture was allowed to stand at room temperature overnight. After removal of solvent at reduced pressure, a liquid residue remained which crystallized on standing for approximately twenty minutes. The solid was soluble in all common solvents with the exception of ligroin, pentane and heptane in which it was partially soluble. After repeated washings with ligroin, two fractions were obtained:
a. ligroin soluble, m.p. 70° to 79° C.;
b. ligroin insoluble, m.p. 129° to 131° C.
The ligroin insoluble fraction analyzed as follows:

Anal. Calc'd. for $C_8H_{21}B_{10}NO_3$: C, 33.45; H, 7.32; B, 37.75; N, 4.75. Found: C, 34.07; H, 7.32; B, 37.11; N, 5.11. Unsat., Found: 104.1%
The ligroin soluble fraction was found to be unreacted hydroxylmethyldekene.

Methacryloyl dekenylmethyl carbamate was found to polymerize on heating above its melting point to a glass-like polymer. It also copolymerized well with petrin acrylate, acryloyl petrin carbamate, and 2-ethylhexyl acrylate. A typical copolymerization using petrin acrylate is described below.

To a small test tube was introduced 2.87 grams (0.01 mole) methacryloyl dekenylmethyl carbamate, 3.25 grams (0.01 mole) petrin acrylate and 1.22 grams (20%) triethylene glycol dinitrate. To this mixture was added 1 mole percent benzoyl peroxide (0.0484 gram) in ether via pipette. After evaporation of the ether under slight vacuum, the test tube was flushed thoroughly with pre-purified nitrogen, stoppered tightly and placed in a thermostated bath at 90° C. A liquid melt was obtained within 5 minutes which polymerized to a rubberlike polymer during the following 6 hours.

In the same way, but with different quantities to compensate for the differences in equivalent weights, i.e., using equimolar quantities, bis(dekenylmethyl) carbinol, didekenyl carbinol, 2-dekenyl ethanol, 3-dekenyl propanol-1, and 4-dekenyl butanol-1 were reacted with methacryloyl isocyanate to form the corresponding carbamates. The compounds obtained were very similar to the compound described hereinbefore and can be homopolymerized, copolymerized, etc. They are all high energy compounds and can be used as hereinbefore described.

As set forth hereinbefore, the compounds of the present invention are prepared by reacting an isocyanate containing a polymerizable vinylidene group with alcohols with high energy content. Thus, vinyl, acryloyl or methacryloyl isocyanates may be reacted with petrin, bis(dekenylmethyl) carbinol, didekenyl carbinol, dekenyl carbinol, 2-dekenyl carbinol, 3-dekenyl propanol-1 or 4-dekenyl butanol-1 to produce the corresponding carbamates.

The compounds of the present invention can be represented by the general formula $$R-NH-\overset{O}{\underset{\|}{C}}-OR'$$

in which R is 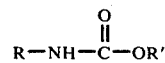

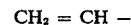

or

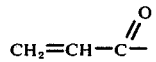

and R' is $(CH_2ONO_2)_3-C-CH_2-$ $(C_2B_{10}H_{11}-CH_2)_2CH-$ $(C_2B_{10}H_{11})_2CH-$ or $C_2B_{10}H_{11}(CH_2)_n-$ in which n is 1, 2, 3, or 4.

I claim:

1. A process for preparing high energy polymerizable monomers which comprises reacting an isocyanate selected from the group consisting of vinyl isocyanate, acryloyl isocyanate and methacryloyl isocyanate with an alcohol selected from the group consisting of trinitratopentaerythritol, bis(dekenylmethyl) carbinol, didekenyl carbinol, dekenyl carbinol, 2-dekenyl ethanol, 3-dekenyl propanol-1 and 4-dekenyl butanol-1.

2. Carbamates of the general formula:

$$R-NH-\overset{O}{\underset{}{C}}-OR',$$

in which R is selected from the group consisting of $CH_2 = CH$ $$CH_2=CH-\overset{O}{\underset{}{C}}-,$$

and $$CH_2=\underset{CH_3}{\overset{}{C}}-\overset{O}{\underset{}{C}}-,$$

and R' is selected from the group consisting of $(CH_2ONO_2)_3C-CH_2-,$ $(C_2B_{10}H_{11}-CH_2)_2CH-,$ $(C_2B_{10}H_{11})_2CH-,$ and $C_2B_{10}H_{11}(CH_2)_n-,$ in which n is 1 to 4.

3. Vinyl petrin carbamate.
4. Acryloyl petrin carbamate.
5. Acryloyl didekenyl carbamate.
6. Vinyl didekenyl carbamate.
7. Vinyl bis(dekenylmethyl) carbamate.
8. Acryloyl bis(dekenylmethyl) carbamate.
9. Homopolymers of carbamates of the general formula $$R-NH-\overset{O}{\underset{}{C}}-OR'$$

in which R is selected from the group consisting of $CH_2 = CH$ $$CH_2=CH-\overset{O}{\underset{}{C}}-,$$

and $$CH_2=\underset{CH_3}{\overset{}{C}}-\overset{O}{\underset{}{C}}-,$$

and R' is selected from the group consisting of $(CH_2ONO_2)_3C-CH_2-$ $(C_2B_{10}H_{11}-CH_2)_2CH-$ $(C_2B_{10}H_{11})_2CH-$ $C_2B_{10}H_{11}(CH_2)_n-$ in which n is an integer from 1 to 4.

10. A homopolymer of acryloyl petrin carbamate.
11. A homopolymer of acryloyl dekenyl carbamate.
12. A homopolymer of acryloyl didekenyl carbamate.
13. A homopolymer of vinyl didekenyl carbamate.
14. A homopolymer of vinyl bis(dekenylmethyl) carbamate.
15. A copolymer of at least one of the monomers of claim 2 with at least one monomer selected from the group consisting of methyl acrylate, ethyl acrylate, butyl acrylate, 2-ethylhexyl acrylate, the higher alkyl esters of methacrylic and ethacrylic acids and mixtures thereof.

* * * * *